United States Patent [19]

Vincent et al.

[11] Patent Number: 4,965,250
[45] Date of Patent: Oct. 23, 1990

[54] PEPTIDE COMPOUNDS HAVING A NITROGENOUS POLYCYCLIC STRUCTURE

[75] Inventors: Michel Vincent, Bagneux; Georges Rémond, Versailles; Claude Cudennec, LaCelle St-Cloud, all of France

[73] Assignee: Adir ET CIE, Neuilly-sur-Seine, France

[21] Appl. No.: 148,027

[22] Filed: Jan. 25, 1988

[30] Foreign Application Priority Data

Feb. 13, 1987 [FR] France .................... 87 01810

[51] Int. Cl.$^5$ .............. A61K 37/02; C07K 5/10
[52] U.S. Cl. ......................... 514/18; 514/885; 530/330
[58] Field of Search ............... 530/330; 514/18, 885

[56] References Cited

U.S. PATENT DOCUMENTS 3,997,516 12/1976 Nishimura ................ 530/330
4,434,095 2/1984 Chipens et al. ............ 530/330
4,720,484 1/1988 Vincent et al. ............ 530/330

FOREIGN PATENT DOCUMENTS 0190058 8/1986 European Pat. Off. .

Primary Examiner—Lester L. Lee
Assistant Examiner—Christina Chan
Attorney, Agent, or Firm—Gordon W. Hueschen

[57] ABSTRACT

Tetrapeptide compounds of general formula:

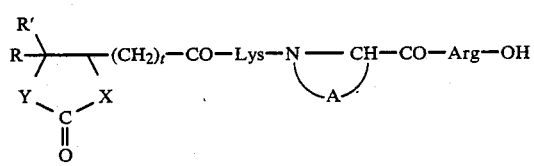

in which
R denotes:
  a hydrogen atom,
  a straight- or branched-chain alkyl radical containing from 1 to 4 carbon atoms,
  an aryl radical such as phenyl or a heterocyclic aromatic radical such as thienyl, optionally substituted with a hydroxy, amino, mercapto, methylthio or lower alkyl group,
  a lower aralkyl radical such as benzyl,
R' denotes a hydrogen atom or a straight- or branched-chain alkyl group containing from 1 to 4 carbon atoms,
X denotes an oxygen atom or an NH group,
Y denotes an oxygen or sulfur atom when X denotes an NH group, or Y denotes an NH group when X denotes an oxygen atom,
t denotes 0 or 1,

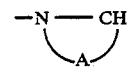

denotes a nitrogen-containing polycyclic structure, their enantiomers, epimers and diastereoisomers, as well as their addition salts with a pharmaceutically acceptable acid or base.

Medicinal products.

14 Claims, No Drawings

PEPTIDE COMPOUNDS HAVING A NITROGENOUS POLYCYCLIC STRUCTURE

The present invention relates to new tetrapeptides, the preparation thereof and the pharmaceutical compositions containing them.

Many natural or synthetic tetrapeptides which modify the biological response are known, and in particular tuftsin (Thr - Lys - Pro - Arg). Some analogs of tuftsin, especially compounds in which the threonine is replaced by a 4-carboxy-2-oxazolidinone radical, have been described by Y. Stabinsky et al. in Int. J. Peptide, Protein Research 1978; 12; 130-138. However, these compounds retain only about half the activity of tuftsin, and have only a weak activity with respect to the antibody response.

Analogs of tuftsin in which the proline is replaced by a nitrogen-containing polycyclic structure are described in European Patent Application No. 0,190,058. These compounds possess, in general, greater activity than that of tuftsin.

The applicant has now discovered analogs of tuftsin in which the proline is replaced by a nitrogen-containing polycyclic structure of the same type as that in the derivatives of European Patent Application No. 0,190,058, (corresponding to U.S. Pat. No. 4,720,484, issued Jan. 19, 1988), and the threonyl residue is cyclized. Surprisingly, these compounds possess an activity which is greater than that of tuftsin and at least equivalent to that of the compounds of Application No. 0,190,058 (corresponding to U.S. Pat. No. 4,720,484, issued Jan. 19, 1988) but, in addition, they have the further advantage of very markedly promoting the antibody response. This characteristic suggests that the compounds of the present invention act by a mechanism different from that of the compounds of the prior art, an especially advantageous property in the therapeutic field in which the$e compound$ may be used.

More specifically, the invention relates to tetrapeptide compounds of general formula:

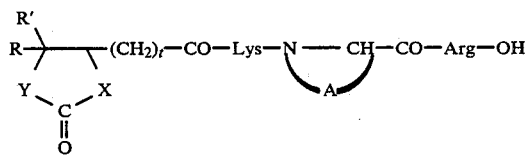

in which
R denotes:
- a hydrogen atom,
- a straight- or branched-chain alkyl radical containing from 1 to 4 carbon atoms,
- an aryl radical such as phenyl or a heterocyclic aromatic radical such as thienyl, optionally substituted with a hydroxy, amino, mercapto, methylthio or lower alkyl group,
- a lower aralkyl radical such as benzyl, R' denotes a hydrogen atom or a straight- or branched-chain alkyl group containing from 1 to 4 carbon atoms, X denotes an oxygen atom or an NH group, Y denotes an oxygen or sulfur atom when X denotes an NH group, or Y denotes an NH group when X denotes an oxygen atom, t denotes 0 or 1, Lys and Arg denote, respectively, lysyl and arginyl residues engaged in peptide bonds,

denotes
a bicyclic structure of the formula:

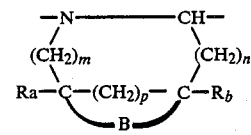

where
m equals 1 or zero,
n and p denote zero, 1 or 2,
$R_a$ and $R_b$ denote a hydrogen atom or can form together a direct bond when p=0,
B denotes an alkylene chain $(CH_2)_q$ where q equals 2, 3 or 4
or an unsaturated structure $(-CH=CH-)_2$ when p=0 and $R_a$ and $R_b$ together form a bond, with the proviso that the sum of m, n, p and
q is an integer between 3 and 6, or
1,2,3,4-tetrahydro-beta-carboline, their enantiomers, epimers and diastereoisomers, as well as their addition salts with a pharmaceutically acceptable acid or base.

Among the compounds of formula I, preference is given at present to those in which the cyclic structure

denotes: indoline, isoindoline, tetrahydroquinoline, tetrahydroisoquinoline, perhydroindol, perhydroisoindol, perhydroisoquinoline, perhydroquinoline, perhydrocyclopenta[b]-pyrrol, 2-azabicyclo[2.2.2]octane, 2-azabicyclo[2.2.1]-heptane or 1,2,3,4-tetrahydro-beta-carboline.

Among acids which may be added to the compounds of formula I to form an additional salt, there may be mentioned, by way of example, hydrochloric, sulfuric, phosphoric, tartaric, malic, maleic, fumaric, oxalic, methanesulfonic, ethanesulfonic, camphoric and citric acids, and the like.

As bases capable of salifying the compounds of formula I, there may be used sodium hydroxide, potassium hydroxide, calcium hydroxide or aluminum hydroxide, alkali metal or alkaline earth metal carbonates or organic bases such as triethylamine, benzylamine, diethanolamine, tert-butylamine, dicyclohexylamine, arginine, and the like.

The invention also encompasses the process for producing the compounds of formula I, wherein a compounds of formula II:

which is obtained as described in European Patent Application No. 0,190,058, published Aug. 6, 1986 or the corresponding U.S. Pat. No. 4,720,484, issued Jan. 19, 1988, in which tBoc denotes a tert-butoxycarbonyl radical and A, with the carbon and nitrogen atoms to which it is attached, has the same meanings as in the formula I, is condensed with N$^\omega$-nitroarginine methyl ester (H-Arg-(NO$_2$)OCH$_3$) or benzyl ester (H-Arg(NO$_2$)OCH$_2$C$_6$H$_5$) to obtain a compound of formula III:

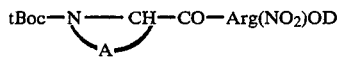   III in which A, with the carbon and nitrogen atoms to which it is attached, has the same meanings as in the formula I, and in which D denotes a methyl or benzyl radical, which is then deprotected with trifluoroacetic acid according to the method described by B. Gutte and K.B. Merrifield (J. Am. Chem. Soc. 1969, 91, 501) to give a compound of formula IV:

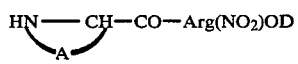   IV in which A, with the carbon and nitrogen atoms to which it is attached, has the same meanings as in the formula I, and in which D has the same meaning as in the formula III,
which is then condensed with N$^{\alpha\text{-}tert\text{-}butoxycarbonyl\text{-}N\omega\text{-}}$benzyloxycarbonyllysine or (tBoc)Lys(Z) to obtain a compound of formula V:

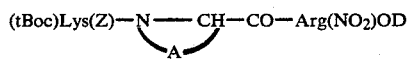   V in which A, with the carbon and nitrogen atoms to which it is attached, has the same meanings as in the formula I and D the same meaning as in the formula III, which is subjected to the action of trifluoroacetic acid and converted to a compound of the formula VI:

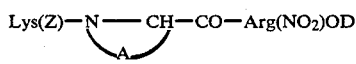   VI in which A, with the carbon and nitrogen atoms to which it is attached, has the same meanings as in the formula I and D the same meaning as in the formula III, which is condensed with a compound of formula VII:

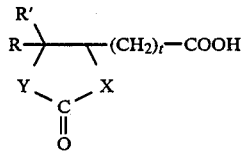   VII in which
R, R', X, Y and t have the same meaning as in the formula I, to lead to a compound of formula VIII

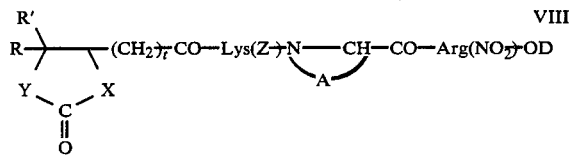   VIII in which A, with the carbon and nitrogen atoms to which it is attached, R, R', X, Y and t have the same meaning as in the formula I and D the same meaning as in the formula III,
which can be either:
when D denotes CH$_3$, deprotected by saponification and then subjected to catalytic hydrogenation,
when D denotes a benzyl group, subjected to catalytic hydrogenation,
to yield a compound of formula I which can, if desired, either be salified with a pharmaceutically acceptable acid or base,
or be separated into its isomers and then, if necessary, salified with a pharmaceutically acceptable acid or base.

The compounds of formula VIII are new and form part of the invention in the same way as the compounds of formula I, constituting the synthesis intermediates of the latter.

The compounds of formula I are endowed with advantageous pharmacological properties.

In particular, the main properties of the compounds of European Patent Application No. 0,190,058 are found in these compounds at a higher or at least comparable level.

In particular, these compounds increase the activity of "natural killer" NK cells. When administered to mice bearing a melanoma, the compounds inhibit the growth of this melanoma to a substantial extent. They promote the immune defenses in animals infected by pathogenic bacterial strains and, unexpectedly by reference to the state of the art, substantially increase the antibody response to sheep antigens in mice, non-specific phagocytosis and delayed hypersensitivity to oxazolone.

These activities are linked to the immunomodulatory properties of the compounds of the invention, which find their application in human or animal therapy in the treatment of cancers, of conditions of viral, bacterial or fungal origin, of autoimmune diseases such as lupus erythematosus or rheumatoid arthritis, and more generally in diseases resulting from a decrease or a disturbance of the natural immune responses of the human or animal body.

In addition, the activity possessed by the compounds of the present invention with respect to the antibody response to sheep red cells in mice suggests that these compounds, while being useful in the same therapeutic indications as the compounds of Application No. 0,190,058, function by a mode of action which is both different from and complementary to that of the compounds of the prior art, thereby making them especially useful in their field of therapeutic application.

The subject of the invention is also the pharmaceutical compositions containing at least one compound of general formula I, or one of its addition salts with a pharmaceutically acceptable acid or base, alone or in combination with one or more pharmaceutically acceptable, non-toxic inert excipients or vehicles.

Among the pharmaceutical compositions according to the invention, there may be mentioned, more especially, those which are suitable for parenteral, per- or transcutaneous, nasal, rectal, perlingual, ocular or respiratory administration, and in particular injectable preparations, aerosols, eye or nasal drops, tablets, sublingual tablets, preparations for sublingual administration, pills, suppositories, creams, ointments, gels for skin application, and the like.

The appropriate dosage varies according to the patient's age and weight, the administration route and the nature of the therapeutic indication and of any associated treatments, and ranges between 1 microgram and 1 gram per dose or per application.

The examples which follow illustrate the invention and in no way limit the latter.

The starting substances are known from the literature.

The melting points indicated are measured according to the micro-Kofler technique. The $^{13}$C nuclear magnetic resonance spectra were recorded using TMS as internal reference, those for $^1$H NMR were generally recorded using CDCl$_3$ as solvent. The mass spectra are produced according to the FAB technique.

EXAMPLE 1:

Cyclo(S)Thr-(S)Lys-(S)ABO-(S)Arg-OH

Cyclo(S)Thr-OH = (trans,L)-4-carboxy-5-methyl-2-oxo-1,3-oxazolidine or (S)-cyclothreonine described by Y. Stabinsky et al. Int. J. Peptide Prot. Res. 1978, 12, 130-138.

STAGE A tBoc(S)ABO-OH or (3S)-2-tert-butoxycarbonyl-2-azabicyclo-[2.2.2]octane-3-carboxylic acid Prepared using the method described in European Patent Application No. 0,190,058 (Example No. 8 - stage A).

STAGE B tBoc(S)ABO-(S)Arg(NO$_2$)-OBzl

Using the method of W. König and R. Geiger (Ber. 1970, 103, 788), couple 0.05 mole of tBoc(S)ABO-OH, obtained in the preceding stage, with 0.05 mole of (S)-N$^\omega$-nitroarginine benzyl ester or (S)-H-Arg(NO2)-OBzl using dimethylformamide as solvent.

tBoc(S)ABO-(S)Arg(NO$_2$)-OBzl is obtained in a 98% yield in the form of an oil, which is used without further treatment in the following stage.

Spectral characteristics in IR (CHCl$_3$ solution)
$\nu$(NH(amide)) = 3400 cm$^{-1}$
$\nu$(CO) = 1700 cm$^{-1}$ (broad)

STAGE C (S)ABO-(S)Arg(NO$_2$)-OBzl

Using the method of deprotection with trifluoroacetic acid in anhydrous methylene chloride described by B. Gutte and R.B. Merrifield (J. Am. Chem. Soc., 1969, 91, 501), starting with 0.0475 mole of tBoc(S)ABO-(S)Arg-(NO$_2$)-OBzl prepared in the preceding stage, (S)ABO-(S)-Arg(NO$_2$)-OBzl is obtained quantitatively in the form of the trifluoroacetate (TFA), whose purity is verified by thin layer chromatography (solvent: CH$_2$Cl$_2$/MeOH, 9:1; Rf = 0.19).

STAGE D tBoc(S)Lys(Z)-(S)ABO-(S)Arg(NO$_2$)-OBzl

By replacing, in stage B above, tBoc(S)ABO-OH by N$\alpha$-tert-butoxycarbonyl-N$\omega$-benzyloxycarbonyl-(S)-lysine (or tBoc(S)-Lys(Z)-OH; 0.0475 mole) and (S)-H-Arg(NO$_2$)-OBzl by (S)ABO-(S)Arg(NO$_2$)-OBzl. TFA (0.0475 mole) prepared in the preceding stage, tBoc(S) Lys(Z)-(S)ABO-(S)Arg(NO$_2$)-OBzl is obtained in the same manner in a 68% yield.

Main $^{13}$C NMR characteristics (DMSO-d$_6$/TMS)
$\delta$ in ppm
C$^\alpha$ Lysine = 50.2
C$^\alpha$ ABO = 59.6
C$^\alpha$ Arg = 51.8

STAGE E (S)Lys(Z)-(S)ABO-(S)Arg(NO$_2$)-OBzl

By deprotecting the tBoc(S)Lys(Z)-(S)ABO-(S)Arg-(NO$_2$)-OBzl with trifluoroacetic acid as described in stage C above, (S)Lys(Z)-(S)ABO-(S)Arg(NO$_2$)-OBzl is obtained quantitatively in the form of trifluoroacetate, whose purity is verified by thin layer chromatography (solvent: CH$_2$Cl$_2$/MeOH, 95:5)

STAGE F

Cyclo(S)Thr-(S)Lys(Z)-(S)ABO-(S)Arg(NO$_2$)-OBzl

By coupling, according to the technique described in stage B above, (S)Lys(Z)-(S)ABO-(S)Arg(NO$_2$)-OBzl with (S)-cyclothreonine (or Cyclo(S)Thr-OH), Cyclo(S)Thr-(S)Lys-(Z)-(S)ABO-(S)Arg(NO$_2$)-OBzl is obtained in the same manner, which is purified by chromatography on silica (60– 230 mesh) using a CH$_2$Cl$_2$/MeOH (96:4) mixture as eluant.

Main $^{13}$C NMR characteristics (DMSO-d$_6$/TMS)
$\delta$ in ppm
C$^\alpha$ Cyclo Thr = 60.0
C$^\alpha$ Lys = 49.0
C$^\alpha$ ABO = 59.7
C$^\alpha$ Arg = 51.5

STAGE G

Cyclo(S)Thr-(S)Lys-(S)ABO-(S)Arg-OH

Subject 0.0012 mole of Cyclo(S)Thr-(S)Lys(Z)-(S)-ABO-(S)Arg(NO$_2$)-OBzl, obtained in the preceding stage, to a catalytic hydrogenation in 80 ml of acetic acid, under a hydrogen pressure of 3 bars in the presence of 400 mg of palladinized charcoal (10% palladium). After evaporation of the solvent under reduced pressure, the amorphous residue is taken up with 5 ml of distilled water, separated by microfiltration and lyophilized.

Cyclo(S)Thr-(S)Lys-(S)ABO-(S)Arg-OH monoacetate is obtained (90% yield)

Spectral characteristics in:
infrared:
$\nu$(CO) : 1750 cm$^{-1}$
mass spectrometry:
FAB+kV spectrum (7 kV)
protonated molecular ion [M+H]+ at M/z = 567
(C$_{25}$H$_{42}$N$_8$O$_7$: MW = 566)

EXAMPLE 2

Cyclo(S)Thr-(S)Lys-(S)THIQ-(S)Arg-OH

STAGE A tBoc(S)THIQ-OH or (3S)-2-tert-butoxycarbonyl-1,2,3,4-tetrahydro-3-isoquinolinecarboxylic acid Prepared according to the method described in Example 1, stage A of European Patent Application No. 0,190,058, replacing (2S,3aS,7aS)-perhydro-2-indolcarboxylic acid by (3S)-1,2,3,4-tetrahydro-3-isoquinolinecarboxylic acid or (S)THIQ-OH.

STAGE B tBoc(S)THIQ-(S)Arg(NO$_2$)-OCH$_3$

Using (S)-N$^\omega$-nitroarginine methyl ester or (S)-H-Arg(NO$_2$)-OCH$_3$ and the tBoc(S)THIQ-OH obtained in the preceding stage, tBoc(S)THIQ-(S)Arg(NO$_2$)-OCH$_3$ is obtained, according to the method of Example 1, in the form of an oil whose purity is verified by thin layer chromatography (solvent: ethyl acetate; Rf=0.2)
Spectral characteristics in IR:
ν(CO) =1740 cm$^{-1}$

STAGE C:

(S)THIQ-(S)Arg(NO$_2$)-OCH$_3$

By replacing tBoc(S)ABO-(S)Arg(NO$_2$)-OBzl in stage C of Example 1 by the tBoc(S)THIQ-(S)Arg-(NO$_2$)-OCH$_3$ obtained in the preceding stage, (S)THIQ-(S)Arg(NO$_2$)-OCH$_3$ is obtained in the same manner in the form of the trifluoroacetate.

Spectral characteristics in NMR ($^1$H)
1.7 ppm : 4H (CH$_2$)
3.2 ppm : 4H (CH$_2$N, CH$_2$-φ)
3.6 ppm : 3H (COOCH$_3$)
4 3 ppm : 4H (N-CH-CO, N-CH$_2$-φ)
7.3 ppm : 4H (phenyl)
7.4 to 10.0 ppm : exchangeable protons.

STAGE D tBoc(S)Lys(Z)-(S)THIQ-(S)Arg(NO$_2$)-OCH$_3$

By replacing (S)ABO-(S)Arg(NO$_2$)-OBzl.TFA in stage D of Example 1 by the (S)THIQ-(S)Arg(NO$_2$)-OCH$_3$.TFA obtained in the preceding stage, tBoc(S)-Lys(Z)-(S)THIQ-(S)Arg-(NO$_2$)-OCH$_3$ is obtained, which is purified by chromatography on silica gel (eluant: ethyl acetate; Rf=0.16). Yield: 66%

STAGE E (S)Lys(Z)-(S)THIQ-(S)Arg(NO$_2$)-OCH$_3$

According to the method used in Example 1, stage C, (S)Lys(Z)-(S)THIQ-(S)Arg(NO$_2$)-OCH$_3$ is obtained in the form of the trifluoroacetate from tBoc(S)Lys(Z)-(S)THIQ-(S)-Arg(NO$_2$)-OCH$_3$.

Thin layer chromatography (solvent: CH$_2$Cl$_2$/MeOH, 90:10; Rf=0.13)

STAGE F

Cyclo(S)Thr-(S)Lys(Z)-(S)THIQ-(S)Arg(NO$_2$)-OCH$_3$

By replacing (S)Lys(Z)-(S)ABO-(S)Arg(NO$_2$)-OBzl.TFA in stage F of Example 1 by (S)Lys(Z)-(S)THIQ-(S)Arg(NO$_2$)OCH$_3$.TFA, Cyclo(S)Thr-(S)Lys(Z)-(S)THIQ-(S)Arg(NO$_2$)-OCH$_3$ is obtained in the form of a thick oil, which is used without further treatment in the following stage.

STAGE G

Cyclo(S)Thr-(S)Lys(Z)-(S)THIQ-(S)Arg(NO$_2$)-OH

Dissolve 0.001 mole of Cyclo(S)Thr-(S)Lys(Z)-(S)-THIQ-(S)Arg(NO$_2$)-OCH$_3$ obtained in the preceding stage in 20 cm$^3$ of methanol, add 10 cm$^3$ of 0.1 N sodium hydroxide and maintain the mixture for 24 hours at room temperature. Concentrate under reduced pressure, take up with 30 cm$^3$ of water and neutralize by adding 10 cm$^3$ of 0.1 N hydrochloric acid. Filter the precipitate, wash with water and then with methylene chloride and dry. Yield: 78%

| | Spectral characteristics: mass spectrometry: | | |
|---|---|---|---|
| FAB$^+$ | m/z | FAB$^-$ | m/z |
| [M + K]$^+$ = | 806 | [M − 2H + Na]$^-$ = | 788 |
| [M − H + 2Na]$^+$ = | 812 | [M − H]$^-$ = | 766 |
| [M + Na]$^+$ = | 790 | [M − H − H$_2$O]$^-$ = | 748 |
| [M + H]$^+$ = | 768 | [M − H − CO$_2$]$^-$ = | 722 |

| | Spectral characteristics: mass spectrometry: | | |
|---|---|---|---|
| FAB$^+$ | m/z | FAB$^-$ | m/z |
| | | [M − H − H$_2$NNO$_2$]$^-$ = | 704 |

STAGE H

Cyclo(S)Thr-(S)Lys-(S)THIQ-(S)Arg-OH

Dissolve 0.0005 mole of Cyclo(S)Thr-(S)Lys(Z)-(S)-THIQ-(S)Arg(NO$_2$)-OH obtained in the preceding stage in 50 cm$^3$ of acetic acid.. Subject to catalytic hydrogenation under a hydrogen pressure of 3 kg/cm$^2$ in the presence of 200 mg of palladinized charcoal (10% palladium). After evaporation of the solvent under reduced pressure, the residue is taken up with 5 cm$^3$ of distilled water, separated by microfiltration and lyophilized. Cyclo(S)Thr-(S)Lys-(S)-THIQ-(S)Arg-OH monoacetate is obtained. Yield: 98%

| | Spectral characteristics: mass spectrometry: | | |
|---|---|---|---|
| FAB$^+$ | m/z | FAB$^-$ | m/z |
| [M$_1$ + H]$^+$ = | 589 | [M$_1$ − H]$^-$ = | 587 |
| [M$_1$ + Na]$^+$ = | 611 | [M$_1$ − H −CO$_2$]$^-$ = | 543 |

EXAMPLE 3

Cyclo(S)Thr-(S)Lys-PHII-(S)Arg-OH

By replacing (3S)-1,2,3,4-tetrahydro-3-isoquinolinecarboxylic acid or (S)THIQ-OH in Example 2, stage A, by perhydro-1-isoindolcarboxylic acid or PHII-OH, the following are successively obtained:
tBocPHII-0H
tBocPHII-(S)Arg(NO$_2$)-OCH$_3$
PHII-(S)Arg(NO$_2$)-OCH$_3$.TFA
tBoc(S)Lys(Z)-PHII-(S)Arg(NO$_2$)-OCH$_3$
(S)Lys(Z)-PHII-(S)Arg(NO$_2$)-OCH$_3$.TFA
Cyclo(S)Thr-(S)Lys(Z)-PHII-(S)Arg(NO$_2$)-OCH$_3$
Cyclo(S)Thr-(S)Lys(Z)-PHII(S)Arg(NO$_2$)-OH
Cyclo(S)Thr-(S)Lys-PHII-(S)Arg-OH
which is lyophilized in the form of the monoacetate

| FAB$^+$ | m/z | FAB$^-$ | m/z |
|---|---|---|---|
| [M$_1$ + H]$^+$ = | 581 | [M$_1$−H]$^-$ = | 579 |
| | | [M$_1$−H−CO$_2$]$^-$ = | 535 |

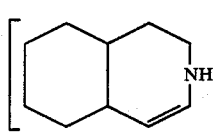 = 124

EXAMPLE 4

Cyclo(2S,3R)AHPA-(S)Lys-(S)ABO-(S)Arg-OH

Cyclo(2S,3R)AHPA-OH or (4R,5S)-2-oxo-4-benzyl-1,3-oxazolidine-5-carboxylic acid, described by H. Umezawa and M. Ohno, European Patent No. 0,156,279, was prepared according to the method of Y. Stabinsky et al. (Int. J. Peptide Prot. Res., 1978, 12, 130–138) from Z(2S,3R)AHPA-OH or (2S,3R)-2-hydroxy-3-benzyloxycarbonyl-amino-4-phenylbutanoic acid described by T. Takita et al. J. Med. Chem., 1977, 20, 510-515.

By replacing Cyclo(S)Thr-OH in Example 1, stage F, by Cyclo(2S,3R)AHPA-OH, the following are successively obtained:
Cyclo(2S,3R)AHPA-(S)Lys(Z)-(S)ABO-(S)Arg-(NO$_2$)-OBzl
Cyclo(2S,3R)AHPA-(S)Lys-(S)ABO-(S)Arg-OH
which is lyophilized in the form of the monoacetate.

Spectral characteristics:
in IR : vs(C =0(oxazolidinone)) : 1760 cm$^{-1}$
in mass spectrometry : FAB+ spectrum
protonated molecular ion[M+H]+ at M/Z : 643

EXAMPLE 5

[(4R)-4-Methyl-2-oxo-1,3-oxazolidinyl-5-carbonyl]-(S)Lys-(S)ABO-(S)Arg-OH

By replacing Z(2S,3R)AHPA-OH by (3R)-2-hydroxy-benzyloxycarbonylaminobutanoic acid described by T. Takita et al. (J. Med. Chem., 1977, 20, 510-515), the following are successively obtained:
(4R)-2-Oxo-4-methyl-1,3-oxazolidine-5-carboxylic acid described by Y. Shimohigashi et al., Bull. Chem. Soc. Jpn., 1979, 52, (3), 949-950.
[(4R)-4-Methyl-2-oxo-1,3-oxazolidinyl-5-carbonyl]-(S)Lys(Z)-(S)ABO-(S)Arg(NO$_2$)-OBzl
[(4R)-4-Methyl-2-oxo-1,3-oxazolidinyl-5-carbonyl]-(S)Lys-(S)ABO-(S)Arg-OH
which is lyophilized in the form of the monoacetate Spectral characteristics:
in IR : vs(CO(oxazolidinone)) 1750 cm$^{-1}$
in mass spectrometry m/z : FAB+ spectrum
[M+H]+ =567
[M+Na]+ =589
[M−H+2Na]+ =611

EXAMPLE 6

CycloGABOB-(S)Lys-(S)ABO-(S)Arg-OH

STAGE A

N-ZGABOB-OH or 3-hydroxy-4-benzyloxycarbonylaminobutanoic acid
Prepared according to the method of Bergmann and Zervas (Ber, 1932, 65, 1192) from 3-hydroxy-4-aminobutanoic acid (GABOB-OH).

STAGE B

CycloGABOB-OH or 5-carboxymethyl-2-oxo-1,3-oxazolidine
Using the method described by Y. Stabinsky et al. (Int. J. Peptide Prot. Res., 1978, 12, 130-138), Cyclo-GABOB-OH is obtained from the NZ-GABOB-OH prepared in the preceding stage.

STAGE C

CycloGABOB-(S)Lys-(S)ABO-(S)Arg-OH
By replacing Cyclo(S)Thr in Example 1, stage F, by CycloGABOB-OH, the following are successively obtained:
CycloGABOB-(S)Lys(Z)-(S)ABO-(S)Arg(NO$_2$)-OBzl
CycloGABOB-(S)Lys-(S)ABO-(S)Arg-OH which is lyophilized in the form of the monoacetate.

EXAMPLE 7

CycloStat-(S)Lys-(S)ABO-(S)Arg-OH

By replacing 3-hydroxy-4-aminobutanoic acid or GABOB-OH in Example 6, stage A, by 3-hydroxy-4-amino-6-methylheptanoic acid or statine (Stat-OH), the following are successively obtained:
Stage A: N-Z-Stat-OH or 3-hydroxy-4-benzyloxycarbonylamino-6-methylheptanoic acid
Stage B: CycloStat-OH or 2-oxo-4-isobutyl-5-carboxymethyl-1,3-oxazolidine
Stage C: CycloStat-(S)Lys-(S)ABO-(S)Arg-OH
which is lyophilized in the form of the monoacetate.

EXAMPLE 8

TZC-(S)Lys-(S)ABO-(S)Arg-OH

By replacing (S)-cyclothreonine in Example 1, stage F, by 2-oxo-4-thiazolidinecarboxylic acid (TZC-OH), the following are successively obtained:
TZC-(S)Lys(Z)-(S)ABO-(S)Arg(NO$_2$)-OBzl
TZC-(S)Lys-(S)ABO-(S)Arg-OH which is lyophilized in the form of the monoacetate.

Spectral characteristics:
mass spectrometry m/z
FAB+ spectrum : [M+H]+ : 569
FAB− spectrum : [M−H]− : 567 [M−H−H$_2$S]− : 533

EXAMPLE 9

Cyclo(S)Thr-(S)Lys-(S)PHI-(S)Arg-OH
By replacing tBoc(S)ABO-OH in Example 1, stage B, by (2S,3aS,7aS)-1-tert-butoxycarbonylperhydro-2-indolecarboxylic acid or tBoc(S)PHI-OH, prepared as described in European Patent Application No. 0,190,058 (Example 1, stage A), and then proceeding as described in Example 1 of the present invention, from stage B to stage G, the following derivative is obtained:
Cyclo(S)Thr-(S)Lys-(S)PHI-(S)Arg-OH, which is lyophilized in the form of the monoacetate.

EXAMPLE 10

DMT-(S)Lys-(S)ABO-(S)Arg-OH
By replacing cyclothreonine in Example 1, stage F, by 5,5-dimethyl-4-carboxy-2-thiozolidinone or DMT-OH, prepared according to F.P. Doyle, D.O. Holland, P, Mamalis and A. Norman (J.C.S 1958, 4605-4614), the following are successively obtained:
DMT-(s)Lys(Z)-(S)ABO-(S)Arg(NO$_2$)-OBzl
DMT-(S)Lys-(S)ABO-(S)Arg-OH
which is lyophilized in the form of the monoacetate.

EXAMPLES 11 to 13

Working as described in Example 1, stage B, but replacing (3S)-2-tert-butoxycarbonyl-2-azabicyclo[2.2.2]octane-3-carboxylic acid or tBoc(S)ABO-OH by (1S)-2-tert-butoxycarbonyl-1-isoindolinecarboxylic acid or tBoc(S)ISI-OH, or by 2-tert-butoxycarbonyl-2-azabicyclo[2.2.1]heptane-3-carboxylic acid or tBocABH-OH, or by (3S)-2-tert-butoxycarbonyl-1,2,3,4-tetrahydro-beta-carboline-3-carboxylic acid or tBoc(S)THC-OH, the following compounds are obtained:
Example 11: Cyclo(S)Thr-(S)Lys-(S)ISI-(S)Arg-OH
which is lyophilized in the form of the monoacetate.
Example 12: Cyclo(S)Thr-(S)Lys-ABH-(S)Arg-OH
which is lyophilized in the form of the monoacetate.
Example 13: Cyclo(S)Thr-(S)Lys-(S)THC-(S)Arg-OH
which is lyophilized in the form of the monoacetate.

EXAMPLES 14 and 15

Working as described in Example 9, and replacing tBoc(S)PHI-OH by 2-tert-butoxycarbonylperhydro-3-isoquinolinecarboxylic acid or tBocPHIQ-OH, or by 1-tert-butoxycarbonylperhydrocyclopenta[b]pyrrole-2-carboxylic acid or tBocPCP-OH, the following compounds are obtained:

Example 14: Cyclo(S)Thr-(S)Lys-PHIQ-(S)Arg-OH which is lyophilized in the form of the monoacetate.

Example 15: Cyclo(S)Thr-(S)Lys-PCP-(S)Arg-OH which is lyophilized in the form of the monoacetate.

EXAMPLES 16, 17 and 18

By replacing Cyclo(2S,3R)AHPA-OH in Example 4 by:

2-oxo-4-phenyl-1,3-oxazolidine-5-carboxylic acid or PHCycloAHPA-0H 2-oxo-4-(2-thienyl)-1,3-oxazolidine-5-carboxylic acid or ThiCycloAHPA-OH 2-oxo-4-(3-hydroxyphenyl)-1,3-oxazolidine-5-carboxylic acid or OHPhCyclo-AHPA-OH the following products are obtained:

Example 16: PHCycloAHPA-(S)Lys-(S)ABO-(S)Arg-OH which is lyophilized in the form of the monoacetate.

Example 17: ThiCycloAHPA-(S)Lys-(S)ABO-(S)Arg-OH which is lyophilized in the form of the monoacetate.

Example 18: OHPhCycloAHPA-(S)Lys-(S)ABO-(S)Arg-OH which is lyophilized in the form of the monoacetate.

EXAMPLE 19

Promotion of NK activity

The compounds according to the invention were tested for their capacity to promote "natural killer" activity. The cells endowed with this capacity form the first line of the body's defense against septic, viral or tumor invasion.

To assess their stimulatory capacity, compounds according to the invention were studied according to the technique of Reynolds et al. 1981 (J. Immunol. 127, 282).

The compounds are injected intravenously at a dose of 20 to 50 $\mu$g/kg into B6D2F1 strain mice.

Three days after the treatment, the animals are sacrificed and their spleen removed and dissociated into its constituent cells, which are then seeded in culture in the presence of YAC-1 tumor cells previously labelled with radioactive chromium. At the end of the incubation period, the destructive capacity of the compounds of the invention is measured by the quantity of chromium released.

By way of example, at a dose of 25 $\mu$g/kg, the compound of Example 1 induces, with respect to the control, a 15% increase in the release of chromium, which is identical to that produced by the compound of Example 8 of European Patent Application No. 0,190,058, whereas tuftsin at a dose if 40 $\mu$g/kg produces a release of only 10%.

EXAMPLE 20

Inhibition of growth of B 16 melanoma.

Melanomas are cancerous tumors which are sensitive to the reaction of the patient's immune system. They hence represent a model of choice for assessing any stimulation of antitumor defense.

The compound according to Example 9 was shown, for example, to be capable of slowing by 45% the growth of mouse B 16 melanoma when the product is administered intraperitoneally at the rate of 20 $\mu$g/kg 3 times per week. Under the same conditions, the percentage obtained with Example 1 of European Patent Application No. 0,190,058 is only 40%, and tuftsin has been shown to be incapable of promoting a decrease in the rate of growth of the grafted tumor.

EXAMPLE 21

Increase in the resistance of animals to infection.

Certain pathogenic bacterial strains inoculated into a healthy host are capable of killing the latter. This is the case, for example, with *Klebsiella pneumoniae*, the agent responsible for pneumonia (Parent, M. et al., Proc. Natl. Acad. Sci. USA, 1978, 75, No. 7, 3395).

The compound of Example 1 behaves identically to the compound of Example 8 of European Patent Application No. 0,190,058, for example, being capable at a dose of 60 $\mu$g per animal of protecting all female Swiss mice weighing 20 to 25 g, into which *Klebsiella pneumoniae* strain 7823 is inoculated IP, against death by infection when the compound is administered 48 hours before the infection. Under the same conditions, tuftsin was capable of saving only 20% of animals.

EXAMPLE 22

Measurement of the antibody response.

The compounds according to the invention were tested for their capacity to increase the antibody response to sheep red cells in mice.

The antibody response is measured in vitro according to Jerne's technique (Science, 1963, 140, 405).

Male C 57 B1/6 mice weighing 23 g on average were treated intravenously with the compounds according to the invention 48 hours before the intraperitoneal inoculation of sheep red cells. Five days later, the production of specific antibodies directed towards sheep red cells is detected in a suspension of spleen cells of these animals.

By way of example, the compound according to Example 1 was shown to be capable, when administered at a dose of 1 mg/kg of increasing the antibody response to sheep red cells in mice by 50%.

By way of comparison, the compound of Y. Stabinsky et al., referred to as [0=C Thr] tuftsin, was capable under the same conditions of increasing this antibody response by a value of only 35%. The corresponding compound of European Patent Application No. 0,190,058, Example 8, proved to be inactive in this test.

EXAMPLE 23

Test of non-specific phagocytosis.

The compounds according to the invention were tested for their capacity to increase non-specific phagocytosis.

This test consists in measuring, after treatment by flow cytometry, the capacity of the polynuclear leukocytes present in the whole blood of dogs to phagocytose latex beads 1.8 $\mu$m in diameter, on the one hand in the absence (control) and on the other hand in the presence of a compound of the invention.

By way of example, the compound according to Example 1 was shown to be capable of increasing by 19% relative to the control the capacity of the polynuclear leukocytes for non-specific phagocytosis, whereas tuftsin, under the same conditions, does not give a significant response.

EXAMPLE 24

Delayed hypersensitivity to oxazolone.

This test consists in sensitizing an animal to oxazolone; seven days later, a delayed hypersensitivity test is performed, on the one hand in the absence (control) and on the other hand after the administration of a compound according to the invention, and in both cases the ear of the sacrificed animal is weighed. The ear is the seat of an inflammatory reaction and its weight depends on the intensity of this reaction. It is found that, after treatment with the compound according to Example 1, the increase in the weight of the ear of the test animals is 11% greater than that in the control batch of animals. Tuftsin does not give a significant response in this test.

EXAMPLE 25

Pharmaceutical compositions.

| Injectable solution | |
|---|---|
| Cyclo(S)Thr—(S)Lys—(S)PHI—(S)Arg—OH: | 0.050 g |
| Water for injections: | 2 cm |
| Skin cream | |
| Cyclo(S)Thr—(S)Lys—(S)ABO—(S)Arg—OH | 5 g |
| Polypropylene glycol | 25 g |
| White vaseline | 10 g |
| Alcohol, 95° strength | 10 g |
| Purified water q.s. | 100 g |

We claim:

1. A compound selected from those of the formula:

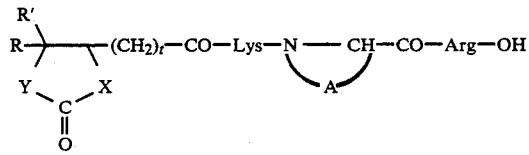

in which

R denotes:
  a hydrogen atom,
  a straight- or branched-chain alkyl radical containing from 1 to 4 carbon atoms,
  phenyl or thienyl, optionally substituted with a hydroxy, amino, mercapto, methylthio or lower alkyl group,
  benzyl,
R' denotes a hydrogen atom or a straight- or branched-chain alkyl group containing from 1 to 4 carbon atoms,
X denotes an oxygen atom or an NH group,
Y denotes an oxygen or sulfur atom when X denotes an NH group, or Y denotes an NH group when X denotes an oxygen atom,
t denotes 0 or 1,
Lys and Arg denote, respectively, lysyl and arginyl residues engaged in peptide bonds,

denotes
a bicyclic structure of the formula:

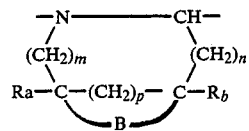

where
m equals 1 or zero,
n and p denote zero, 1 or 2,
$R_a$ and $R_b$ denote a hydrogen atom or can form together a direct bond when p=0,
B denotes an alkylene chain $(CH_2)_q$ where q equals 2, 3 or 4
or an unsaturated structure (—CH=CH—)$_2$ when p=0 and $R_a$ and $R_b$ together form a bond, with the proviso that the sum of m, n, p and q is an integer between 3 and 6, or 1,2,3,4-tetrahydro-beta-carboline, or an enantiomer, epimer, or diastereoisomer thereof, or an addition salt of any of the foregoing with a pharmaceutically-acceptable acid or base.

2. A compound as claimed in claim 1, in which the cyclic structure

denotes indoline, isoindoline, tetrahydroquinoline, tetrahydroisoquinoline, perhydroindol, perhydroisoindol, perhydroquinoline, perhydroisoquinoline, perhydrocyclopenta[b]-pyrrol, 2-azabicyclo[2.2.2]octane, 2-azabicyclo[2.2.1]-heptane or 1,2,3,4-tetrahydro-beta-carboline.

3. A compound as claimed in claim 1, in which the cyclic structure

denotes perhydroindol or 2-azabicyclo[2.2.2]octane.

4. Compound of claim 1 being Cyclo(S)Thr-(S)-Lys-(S)ABO-(S)Arg-OH or an addition salt thereof with a pharmaceutically-acceptable acid or base.

5. Compound of claim 1 being Cyclo(S)Thr-(S)Lys-(S)PHI-(S)Arg-OH or an addition salt thereof with a pharmaceutically-acceptable acid or base.

6. Compound of claim 1 being Cyclo(S)Thr-(S)Lys-(S)THIQ-(S)Arg-OH or an addition salt thereof with a pharmaceutically-acceptable acid or base.

7. Compound of claim 1 being Cyclo(S)Thr-(S)Lys-PHII-(S)Arg-OH, or an enantiomer or diastereoisomer thereof, or an addition salt of any of the foregoing with a pharmaceutically-acceptable acid or base.

8. Compound of claim 1 being Cyclo(2S, 3R)AHPA-(S)Lys-(S)ABO-(S)Arg-OH or an addition salt thereof with a pharmaceutically-acceptable acid or base.

9. Compound of claim 1 being [(4R)-4-Methyl(-2-oxo-1,3-oxazolidinyl-5-carbonyl]-(S)Lys-(S)ABO-(S)Arg-OH, or an enantiomer thereof, or an addition salt of any of the foregoing with a pharmaceutically-acceptable acid or base.

10. Compound of claim 1 being CycloGABOB-(S)Lys-(S)ABO-(S)Arg-OH, or an enantiomer thereof, or an addition salt of any of the foregoing with a pharmaceutically-acceptable acid or base.

11. A pharmaceutical composition useful for stimulation of the natural immune system containing as active principle an effective amount of at least one compound as claimed in claim 1, in combination with one or more pharmaceutically-acceptable excipients or vehicles.

12. A composition as claimed in claim 11, in which the cyclic structure of the compound of Formula I NA'-CH denotes perhydroindol or 2-azabicyclo[2.2.2]octane, or an enantiomer, epimer or diastereoisomer thereof, or an addition salt or any of the foregoing with a pharmaceutically-acceptable acid or base.

13. A method for treating a living animal in need of stimulation of the natural immune system comprising the step of administering to the said living animal an amount of a compound of claim 1 which is effective for such stimulation.

14. A method as claimed in claim 13, in which the cyclic structure of the compound of Formula I

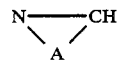

denotes perhydroindol or 2-azabicyclo[2.2.2]octane, or an enantiomer, epimer, or diastereoisomer thereof, or an addition salt of any of the foregoing with a pharmaceutically-acceptable acid or base.

* * * * *